(12) United States Patent
Dupoy et al.

(10) Patent No.: US 9,359,631 B2
(45) Date of Patent: Jun. 7, 2016

(54) METHOD FOR OBSERVING A SAMPLE (75) Inventors: Mathieu Dupoy, Grenoble (FR); Pierre Joly, Grenoble (FR); Frédéric Mallard, Voreppe (FR); Pierre Marcoux, Voreppe (FR); Raphaël Mathey, Grenoble (FR); Armelle Novelli-Rousseau, Seyssins (FR)

(73) Assignees: Commissariat a L'Energie Atomique et aux Energies Alternatives, Paris (FR); Biomerieux, Marcy-l'Etoile (FR)

( * ) Notice: Subject to any disclaimer, the term of this patent is extended or adjusted under 35 U.S.C. 154(b) by 0 days.

(21) Appl. No.: 14/000,813

(22) PCT Filed: Feb. 16, 2012

(86) PCT No.: PCT/IB2012/050721
§ 371 (c)(1),
(2), (4) Date: Sep. 12, 2013

(87) PCT Pub. No.: WO2012/114237
PCT Pub. Date: Aug. 30, 2012

(65) Prior Publication Data
US 2013/0344532 A1 Dec. 26, 2013

(30) Foreign Application Priority Data
Feb. 21, 2011 (FR) ..................................... 11 00522

(51) Int. Cl.
| | |
|---|---|
| *C12Q 1/04* | (2006.01) |
| *G01N 21/63* | (2006.01) |
| *G01N 21/43* | (2006.01) |
| *G01N 21/41* | (2006.01) |
| *G01N 21/64* | (2006.01) |
| G01N 21/65 | (2006.01) |
| G01N 21/03 | (2006.01) |

(52) U.S. Cl.
CPC .............. *C12Q 1/04* (2013.01); *G01N 21/6486* (2013.01); *G01N 21/65* (2013.01); *G01N 2021/035* (2013.01)

(58) Field of Classification Search
None
See application file for complete search history.

(56) References Cited

U.S. PATENT DOCUMENTS

| | | |
|---|---|---|
| 6,391,578 B2 | 5/2002 | Williams et al. |
| 2004/0109038 A1 | 6/2004 | Newsome et al. |
| 2005/0221339 A1 | 10/2005 | Griffiths et al. |
| 2009/0161100 A1* | 6/2009 | Minot et al. ................. 356/244 |

FOREIGN PATENT DOCUMENTS

| | | |
|---|---|---|
| JP | 2008-249446 A | 10/2008 |
| WO | WO-82/02562 | 8/1982 |

OTHER PUBLICATIONS

Life Technologies. Epifluorescence microscope basics. Datasheet [online]. Thermo Fisher Scientific, Inc., Copyright 2015 [retrieved on Jan. 24, 2015]. Retrieved Internet: <URL: https://www.lifetechnologies.com/ . . . ing center/molecular-probes-school-of-fluorescence/fundamentals-of-fluorescence-microscopy/epifluorescence-microscope-basics.html>pp. 2-4.*
Rost, F. et al. Immersion.In: Photography with a Microscope. Cambridge University Press (publishers). Copyright 2000. F.W.D. Rost and R.J. Oldfield. Ed.: F. Rost and R. Oldfield.Cambridge, U.K. p. 71.*
Sacconi, L. 2006. Cell Imaging and Manipulation by Nonlinear Optical Microscopy. Cell Biochemistry and Biophysics 45:289-302. specif. pp. 294-296.*
Eldridge, M. L., et al.; "*Saccharomyces cerevisiae BLYAS, a New Bioluminescent Bioreporter for Detection of Androgenic Compounds*;" Applied and Environmental Microbiology, vol. 73, No. 19; pp. 6012-6018; dated 2007; retrieved on Sep. 11, 2013 from <https://www.researchgate.net/go.To.html?u=http%3A%2F%2Fwww.ncbi.nlm.nih.gov%2Fpmc%2Farticles%2FPMC2074987%2Fpdf%2F0589-07.pdf&ev=pub_int_doc_dlext>.
Rotman, B.; "*Measurement of activity of single molecules of*β-*D-Galactosidase*;" Proceedings of the Natl Acad Sci USA, vol. 47, No. 12; pp. 1981-1991; dated Dec. 1961; retrieved on Sep. 11, 2013 from <http://www.ncbi.nlm.nih.gov/pmc/articles/PMC223251/pdf/pnas00216-0111.pdf>.
Theberge, A. B., et al.; "*Microdroplets in Microfluidics: An Evolving Platform for Discoveries in Chemistry and Biology*;" Angew Chem Int Ed, vol. 49, No. 34; pp. 5846-5868; dated Jun. 2010; retrieved on Sep. 11, 2013 from <https://www.researchgate.net/publication/44696547_Microdroplets_in_microfluidics_an_evolving_platform_for_discoveries_in_chemistry_and_biology/file/3deec521260d289940.pdf?ev=srch_pub_xdl>.
International Search Report and Written Opinion for Application No. PCT/IB2012/050721; dated May 10, 2012.

* cited by examiner

Primary Examiner — Renee Claytor
Assistant Examiner — Sharon M Papciak
(74) Attorney, Agent, or Firm — Alston & Bird LLP (57) ABSTRACT

A method for observing a sample is provided. The method includes the steps of: a) providing a volume (G, V) of a substantially transparent medium having a first refractive index ($n_{int}$) and having a first surface (S1) that is convex, rounded, or faceted, and a second substantially planar surface (S2), the first surface separating the volume from a surrounding medium (MA) having a second refractive index ($n_{est}$) that is lower than the first index, the sample to be observed being contained inside the volume or being deposited on the first surface; b) observing the sample through the second substantially planar surface; and c) determining the presence of a substance or an object in the sample by detection during step b), a ring of light that correlates with the volume.

11 Claims, 6 Drawing Sheets

METHOD FOR OBSERVING A SAMPLE

FIELD

The invention relates to a method for observing a sample, in particular for biological or chemical applications such as detecting or counting microorganisms and the study of the kinetics of chemical reactions.

BACKGROUND

A method in accordance with a preferred embodiment is based on the use of a microdroplet for containing the sample to be observed, or itself constituting said sample. The article by A B Theberge et al, "*Microdroplets in Microfluidics: An Evolving Platform for Discoveries in Chemistry and Biology*", Angew Chem Int Ed 2010, 49, 5846-5868, presents a review of microfluidics techniques based on the use of liquid microdroplets for a variety of applications in chemistry and in biology. The term "microdroplets" means droplets with a diameter (or, more generally, principal dimension) in the range 1 µm to 100 µm.

Document US 2005/0221339 describes a method for the optical detection of chemical components in microdroplets manipulated in a microfluidics system.

The article by B Rotman, "*Measurement of activity of single molecules of β-D-Galactosidase*", Proceedings of the Natl Acad Sci USA, 1961, 47, pp 1981-1991, describes a method for the detection of isolated molecules of an enzyme. In that method, an aqueous solution containing the enzyme (highly diluted) and a fluorogenic substrate for that enzyme is sprayed into a small volume of silicone oil confined between two microscope slides. Given that the oil is less dense than water and immiscible therewith, the solution forms microdroplets that are deposited on the upper surface of the lower microscope slide. Next, the droplets are analyzed by microfluorimetry with the aid of a microscope. The droplets containing at least one molecule of the enzyme appear as luminous disks, while the droplets containing none appear in the form of luminous rings.

The principal limitation to such methods resides in the low intensity of the light emitted by fluorescence. Similar problems arise when the light that is diffused (elastic or Raman diffusion) by an object of microscopic dimensions contained in a droplet is to be observed.

SUMMARY

The aim of the invention is to overcome this limitation by proposing a configuration for observing a sample that improves the collecting efficiency of light emitted or diffused by the sample. However, the invention is not limited to using a liquid droplet, but encompasses the case in which the liquid droplet is replaced by a volume of a solid medium or a gel.

Thus, in one aspect, the invention provides a method for observing a sample, comprising the steps consisting of:
a) providing a volume of a substantially transparent medium having a first refractive index $n_{int}$ and having a first convex, rounded or facetted surface, and a second substantially planar surface, said first surface separating said volume from an ambient medium having a second refractive index $n_{ext}$, the sample to be observed being constituted by said volume or disposed within it or deposited on said first surface; and
b) observing said sample;
characterized in that:
 during step b), said sample is observed through said second substantially planar surface;
and in that:
 said second refractive index is lower than said first index.

The method may comprise a step c) for determining the presence of a substance or an object in the sample as a function of the results of observation of said sample during step b). In particular, the object may be a biological species such as a microorganism, for example a bacterium, a yeast, a fungus, a virus, etc. A substance to be detected may, for example, be dissolved or dispersed in a transparent or translucent medium.

The sample may be a liquid, for example a biological liquid, an ionic liquid, an aqueous solution or a gel. In the case of a gel, the viscosity may, for example, be in the range 1 cP (centipoise) to 1000 cP, i.e. in the range $10^{-3}$ Pa·s to 1 Pa·s.

As will be explained in more detail below, the fact that the refractive index of the ambient medium is lower than that of the volume ensures partial guidance of the light emitted or diffused by the sample along said first convex surface ("bowl of light"), which improves the efficiency of its detection on the second planar surface side. In contrast, in the prior art (see in particular B Rotman's article cited above), "reverse emulsions" of aqueous solutions in an oil with a higher optical index are usually used, and/or the sample is observed via the convex face.

Typically, the volume may have a diameter or principal dimension in the range 1 µm to 1 mm, preferably in the range 10 to 500 µm.

According to various embodiments of the invention:
 said volume may be substantially hemispherical in shape. This is in fact the geometry that maximizes collection of the light emitted or diffused by the sample;
 said volume may be a droplet adhered to a transparent substrate forming said second substantially planar surface;
 said step a) may comprise producing a plurality of droplets forming said volumes at least some of which contain at least one object or a substance to be detected; and said step b) may comprise simultaneously observing a plurality of said droplets;
 in contrast, said volume may be a solid volume, in which case the sample may be constituted by a layer deposited on its first surface. Advantageously, said layer may be a functionalized layer, sensitive to an analyte that might be contained in said ambient medium. When the volume is solid, the sample may also be a liquid or viscous sample placed in contact with the first surface of the volume;
 said volume may be formed from a material that is sensitive to an analyte that might be contained in said ambient medium;
 said ambient medium may be air;
 said step b) may comprise an operation of illuminating said volume. Preferably, said illumination may be carried out through said substantially planar second surface so that it can in turn benefit from the light guiding effect mentioned above. In different variations:
 said step b) may include detecting an optical signal, for example fluorescence. In this case, said step b) may be carried out by epifluorescence microscopy;
 said step b) may comprise detection of a Raman diffusion signal;
 said step b) may be carried out by reflection or transmission microscopy.

BRIEF DESCRIPTION OF THE DRAWINGS

Further characteristics, details and advantages of the invention will become apparent from the description made with reference to the accompanying drawings, given by way of example, which respectively represent.

DETAILED DESCRIPTION

Figure 1:
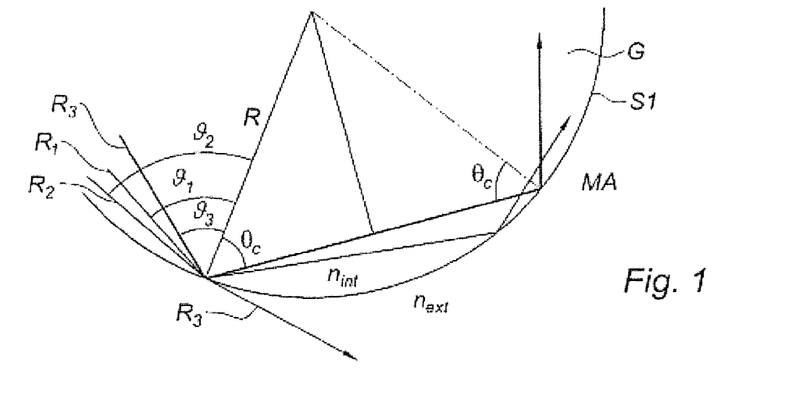
in FIG. 1, the paths of various rays of light propagating at the interface between a droplet and an ambient medium with a lower refractive index such as air.

FIG. 1 illustrates the physical phenomenon forming the basis of the invention. Consider a droplet G of a liquid with a refractive index (real) $n_{int}$, immersed in an ambient medium MA with a refractive index (also real) $n_{ext} < n_{int}$. In the case of a droplet of water in air, we have $n_{int} = 1.33 < n_{ext} = 1$.

Following surface tension effects the droplet takes on a substantially spherical or a truncated spherical shape with diameter R; if R is of the order of a few micrometers, the deformations induced by the force of gravity can in practice be ignored.

FIG. 1 shows three rays of light R1, R2 and R3 that propagate inside the droplet G and which meet its surface S1 with an angle of incidence $\theta_1$, $\theta_2$ and $\theta_3$ respectively. Conventionally, the angle of incidence is defined as the angle formed between the ray and the normal to the surface.

All of the rays that meet the surface S1 with an angle of incidence of more than the critical angle $\theta_c$, given by $$\sin(\theta_c) = \frac{n_{ext}}{n_{int}},$$

undergo total reflection and remain trapped inside the droplet. In the example of FIG. 1, this is the case for rays R1 (for which $\theta_1 = \theta_c$) and R2 (for which $\theta_2 > \theta_c$), while ray R3 leaves the droplet since $\theta_3 < \theta_c$.

Simple geometric reasoning can show that the rays undergoing total reflection remain confined in the proximity of the surface S1 of the droplet and cannot get any closer to its center than a distance of less than $$r = R \frac{n_{ext}}{n_{int}}.$$

Figure 2A:
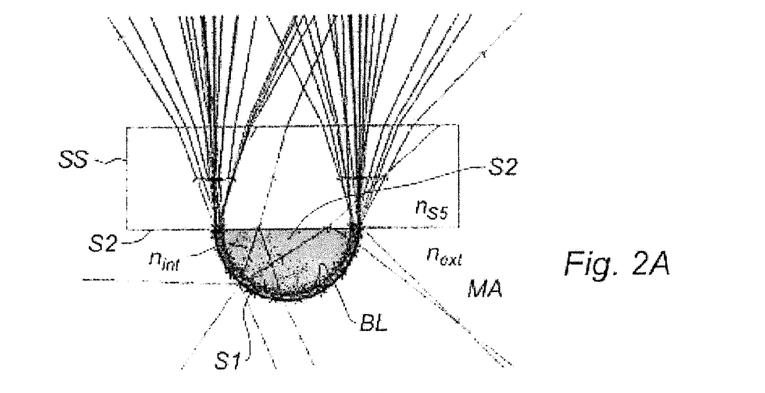
in FIGS. 2A and 2B, a ray pattern obtained from a point of the droplet located close to said interface.

In order to understand how this effect can assist the observation of objects such as microorganisms or fluorescent molecules, consider the situation illustrated in FIG. 2, showing a hemispherical droplet G adhered to a transparent support SS and immersed in a medium MA such as air. As in the previous case, $n_{ext} < n_{int}$; the refractive index $n_{SS}$ of the substrate may be less than or greater than $n_{int}$; preferably, it will not be too high (for example, less than or equal to $2n_{int}$) so that it does not itself trap light. Rays of light are emitted by a fluorescent molecule located at a point close to the hemispherical surface S1 of the drop (S2 indicates the contact surface with the substrate). It can be seen that a significant portion of these rays are guided by the air-water interface into a layer taking the shape of a "bowl of light", BL. These rays leave the drop at the planar surface S2 in a zone with an annular shape (which may also be known as a circular ring) included between an inner radius $$r = R \frac{n_{ext}}{n_{int}}$$

and an outer radius R. It will be appreciated that this improves the light collection efficiency. The thickness of the bowl of light BL, which may also be designated by the term spherical envelope, is equal to R−r.

Figure 2B:
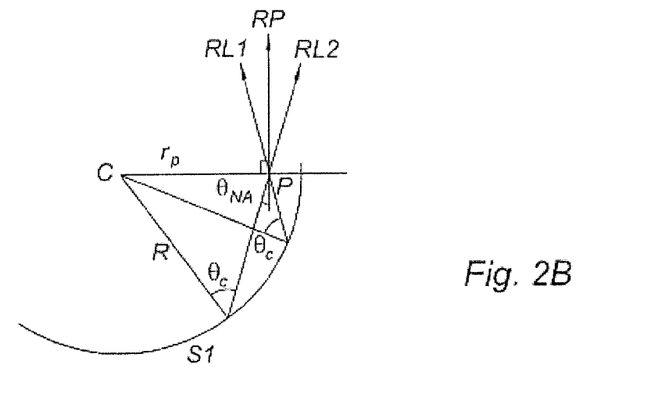

In order to determine the angular extent of the beam that is routed into the bowl of light, FIG. 2B concerns rays passing through a fixed point P located at a distance $r_P$ from the center C. If $r_P$ satisfies the condition $r < r_P < R$, then it can be shown that two rays RL1 and RL2 exist that intercept the circle S1 at the critical angle of incidence $\theta_c$ and the bisector of RL1 and RL2, denoted RP, is orthogonal to CP. The angle $\theta_{NA}$ between RP and RL1 or RL2 is such that $$\frac{\sin\theta_c}{r_P} = \frac{\sin(90° - \theta_{NA})}{R},$$

i.e. $\theta_{NA} = \cos^{-1}\left(\frac{n_{ext}}{n_{int}} \times \frac{R}{r_P}\right).$ In terms of optical geometry, this indicates that inside the volume G, the beam formed by the rays passing through P have a principal ray RP (perpendicular to CP) and an aperture angle $\theta_{NA}$. The limiting values for $\theta_{NA}$ are: 0 (when $r_P = r$) and $\theta_{NAMax} = 90° - \theta_c$ (when $r_P = R$). Thus, the beam has the largest numerical aperture at the edge of the ring.

Figure 3:
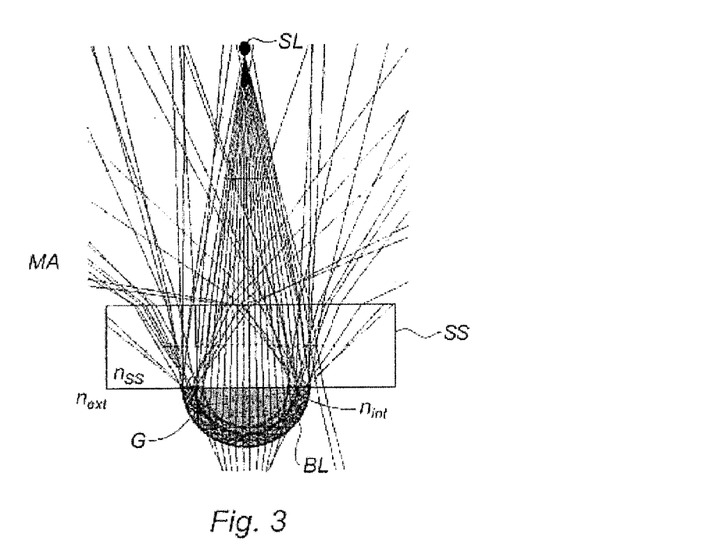
in FIG. 3, a ray pattern showing the confinement of the light entering into such a droplet in proximity to its periphery in the plane passing through the light source and perpendicular to said second surface.

FIG. 3 illustrates the reciprocal situation, in which a light source SL illuminates the droplet G through the substrate SS. Preferably, illumination is such that there is no mask disposed between the light source SL and the transparent substrate SS. In addition, the substrate SS and the droplet G are not illuminated in a "dark field" configuration. In this figure, the rays that penetrate into the droplet via the annular zone cited above from the planar surface S2 remain trapped in the "bowl of light" BL. A sample or a portion of a sample located inside this "bowl" is illuminated far more effectively than if light trapping had not occurred.

Figure 4A:
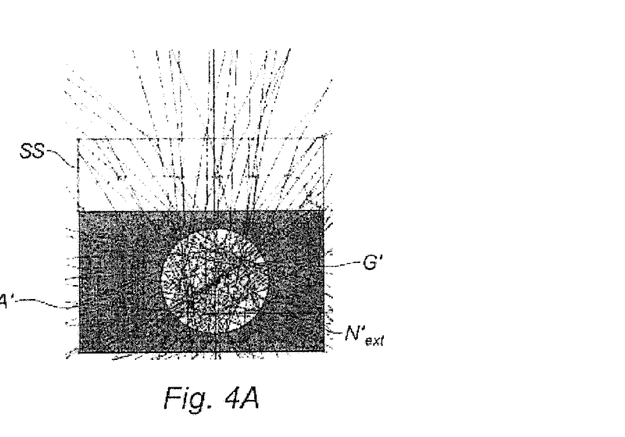
in FIGS. 4A and 4B, two ray patterns for the observation configuration described in the article by B Rotman cited above.
Figure 4B:
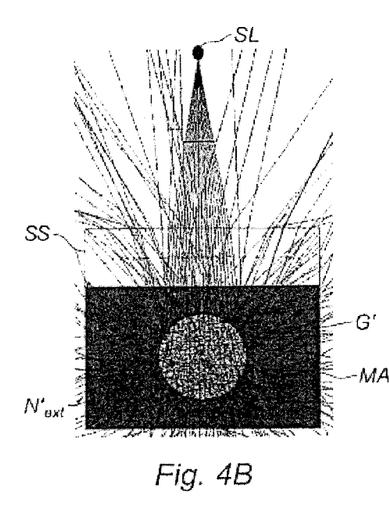

This effect of confining the rays of light is dependent on the condition $n_{ext} < n_{int}$, as can be seen in FIGS. 4A and 4B, which concern the opposite situation in which $n'_{ext} > n'_{int}$ (case of a water droplet G'—$n_{int}' \approx 1.33$—in a bath MA' of silicone oil—$n_{ext}' \approx 1.44$). It can be seen in these figures that in this case, neither the rays emitted by an external source SL nor those obtained from a point on the droplet surface remain trapped.

Figure 5:
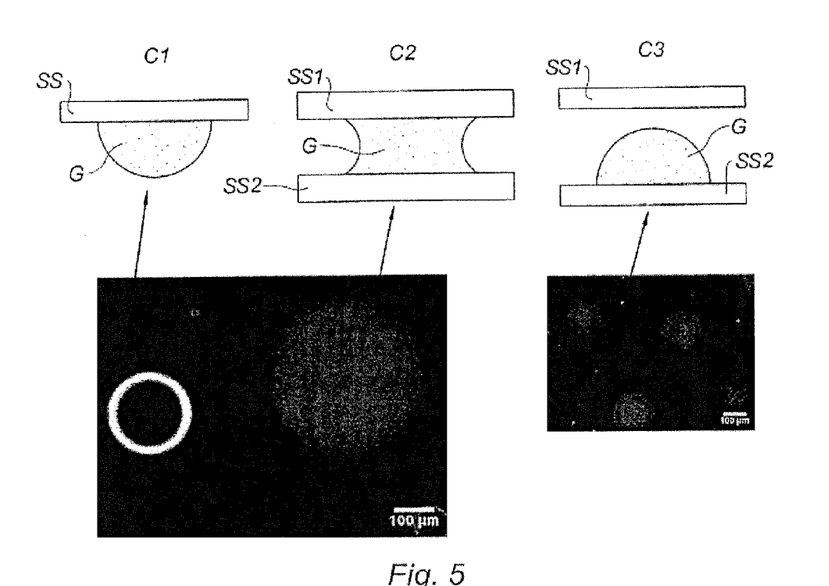
in FIG. 5, a comparative test illustrating the advantages of the invention.

FIG. 5 can be used to compare the observation configuration of the invention (C1) with two other configurations: a droplet squashed between a—lower-microscope slide (SS2) and an—upper-cover slip (SS1) (C2) and a droplet deposited on a slide and observed from its convex surface side (C3). In all cases, the droplet is constituted by a 5 µM aqueous solution of a fluorophore 4MU (4-methylumbelliferone). The droplets are observed by epifluorescence microscopy, i.e. with excitation and detection from the top. It can be seen that the configuration C1 of the invention can be used to observe very luminous rings, while in the other configurations, the fluorescent droplet appears as a very low luminosity disk which is difficult to see against the background. Experimental measurements showed that the configuration of the invention can enhance the quantity of light collected by a factor of 20 compared with the "water in oil" configuration used by Rotman. The term "quantity of light" means the quantity of light measured over the whole of the drop, comprising both the luminous ring and the central zone, which is much darker. In contrast, if only the light emitted in a circular ray with a radius in the range $$r = R \frac{n_{ext}}{n_{int}}$$

and R is taken into account, the gain may even reach a factor of 70.

The case of a hemispherical droplet is optimal, but the confinement effect persists even if the surface S1 deviates from this nominal shape. In order to quantify the deviations that are tolerable, we must first consider that the surface S1 might not be exactly a portion of a sphere, and secondly, that the volume G, which is generally spherical, might not be truncated exactly in the middle or by an exactly planar surface.

Figure 12A:
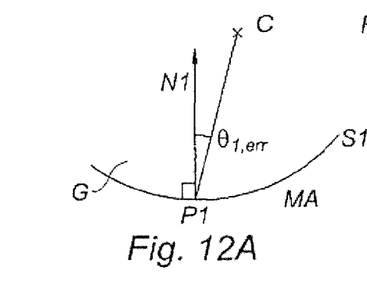
FIGS. 12A to 12D illustrate the consequences of deviations from the shape of the volume with respect to a hemisphere.

As can be seen in FIG. 12A, at each point P1 of S1, the normal N1 is defined, oriented towards the interior of the drop (from MA to G). The angular deviation with respect to a sphere with center C is defined as follows: $\theta_{1,err}$ (P1, C); it is the angle between N1 and the straight line (P1, C). The center of the spherical surfaces which fit S1 the best is the point C1 that minimizes $$\iint_{P1 \in S1} \theta_{1,err}(P1, C1) dS1$$

(the angles are not oriented, and thus their values are always positive). Once this point has been found, termed the angular center of S1, a maximized angular deviation $\theta_{1,errMax}$ is defined as the maximum of $\theta_{1,err}$(P1, C) for P1 over the whole of the surface S1.

The size of the effect of confining the light at the periphery of the drop exploited by the invention depends on the relative thickness of the "bowl of light" which is $$\varepsilon = \frac{R-r}{R}.$$

In the case of a spherical surface:

$$\varepsilon = 1 - \frac{n_{ext}}{n_{int}}.$$

Preferably, in order to remain in the field of optical geometry, the thickness of the bowl of light must be greater than the wavelength λ of the light. In other words, preferably, R−r≥λ. For a wavelength λ of 500 nm, and assuming $n_{ext}$=1.33 (refractive index of water) and n=1 (refractive index of air), this condition results in R≥2 µm. In addition, in general, the diameter of a droplet G will be more than 2 µm, or even 4 µm.

Figure 12B:
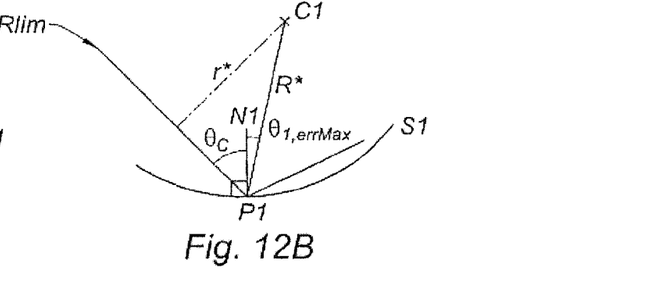

As illustrated in FIG. 12B in the case of a surface S1, which is not entirely spherical as characterized above, a limiting ray for total reflection, Rlim, in the worst case of angle composition will make an angle ($\theta_c + \theta_{errMax}$) with the segment [P1, C1]. The relative thickness of the bowl of light in this configuration is $$\varepsilon^* = \frac{R^* - r^*}{R^*} = 1 - \sin(\theta_c + \theta_{errMax}).$$

Using the numerical values corresponding to a drop of water in air ($n_{int}/n_{ext}$=4/3, i.e. $\theta_c$=48.6°), it will be found that $\theta_{errMax}$=4.5°, corresponding to a relative reduction in the ring width of 20%. If a relative reduction in the ring width of 50% is tolerated, then angular deviations on S1 with respect to a sphere of up to 12.5° can be tolerated.

Figure 12C:
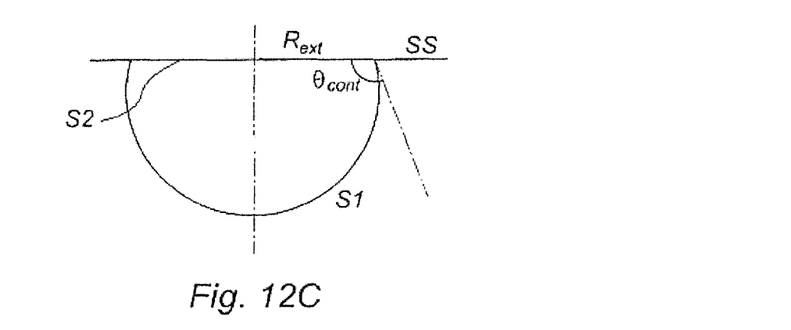
Figure 12D:
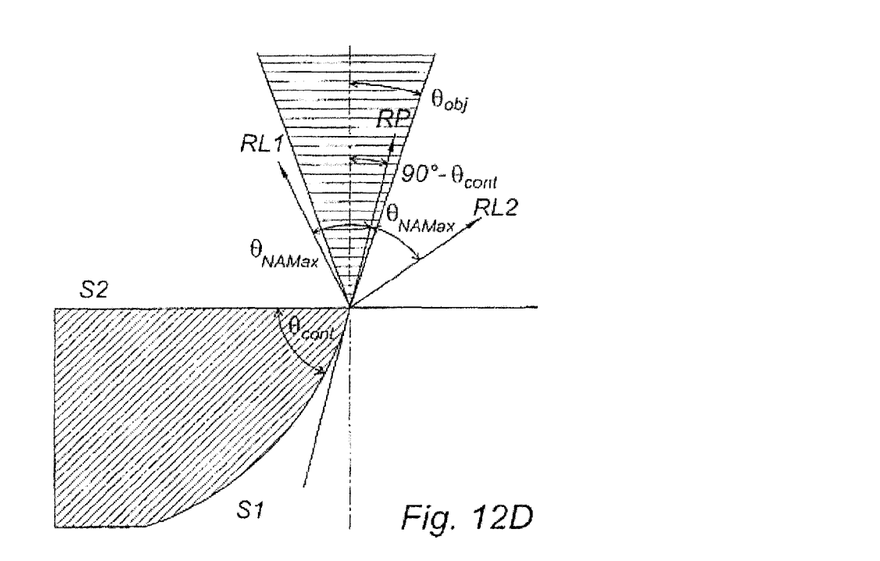

A contact angle (between S1 and S2), denoted $\theta_{cont}$, which is not 90° means that the principal ray (RP) of the beam of light confined in the bowl of light is no longer perpendicular to S2 at the time it passes through this surface (see FIG. 12C). The criterion for defining the tolerance is that the whole of the numerical aperture of the observation system (peak half angle cone $\theta_{cont}$ hatched in FIG. 12D) is included in the aperture angle of the guided beam, which is limited by RL1 and RL2. Considering just the medium with index $n_{int}$, the aperture angle of the guided beam is $\theta_{NAMax}$=(90°−$\theta_c$), i.e. 41.4° for $n_{int}/n_{ext}$=4/3 (water-air pairing). For the hatched triangle to be included between RL1 and RL2, then, it is necessary for |90°−$\theta_{cont}$|<$\theta_{NAMax}$−$\theta_{obs}$. For light to be collected by a microscope objective with a typical numerical aperture of NA=0.5, we have an aperture angle $\theta_{obs}$ in the medium with index $n_{int}$ of 22° (NA=$n_{int}$ sin $\theta_{obs}$). With this visualizing system and for $n_{int}/n_{ext}$=4/3, it is found that $\theta_{cont}$ is in the range 70° to 110°.

The droplet G may be replaced by a convex volume with a generally rounded shape of a solid or a gel. In these cases, the surface S2 may comprise facets (in a sufficiently great number, by way of indication at least 10 and preferably 20 or more, to be able to qualify the surface as "generally rounded").

The ambient medium does not necessarily have to be air, although this choice is advantageous since it can be used to maximize the difference $n_{int} - n_{ext}$. In fact, the efficiency of the light confinement effect is greater as the difference between the refractive indices increases; preferably, $n_{int} \geq 1.1 \times n_{ext}$.

Figure 6:
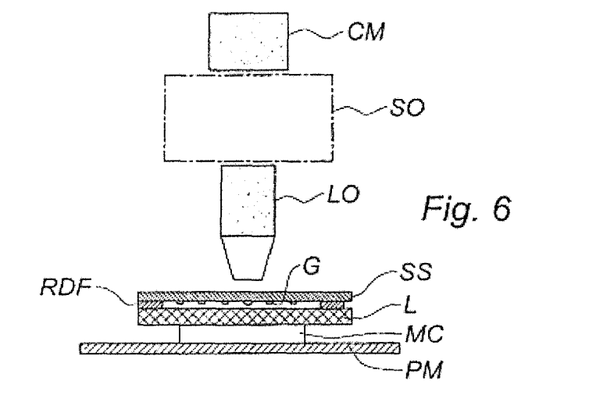
in FIG. 6, an experimental setup for carrying out a method in accordance with the invention.

FIG. 6 shows an experimental setup for carrying out the method of the invention.

The substrate SS is a 170 µm thick glass slip cover that is silanized in order to render it hydrophobic. An aqueous solution containing the objects or substances to be detected (microorganisms, fluorescent molecules in solution, etc.) is sprayed onto this slip cover, forming droplets with a radius in the range from a few µm, for example 2 µm or 4 µm, to 200 µm, i.e. volumes of about 1 µL to 10 nL. Because of the hydrophobic treatment of the surface, these droplets have a contact angle in the range 92° to 96° (the ideal hemispherical case corresponds to a contact angle of 90°). Computer simulations have been able to show that the gravitational force does not deform the droplets, irrespective of the orientation of the slip cover.

It should be noted that several techniques other than simple spraying may be used in order to form the droplets, in particular if they are to be mono-disperse. Examples that may be cited are deposition by spotting, i.e. by depositing a droplet (or a plurality of droplets) using a micropipette, for example piezo-electric, which can be controlled by an automated device, by dispersion or by microstructuring hydrophilic/hydrophobic zones as described in document U.S. Pat. No. 6,391,578. Gel droplets may be deposited using the technique described in document WO 82/02562, in which a suspension is fractionated in the liquid state then gelled.

It is also possible to envisage using one or more hemispherically shaped cups intended to be filled with a liquid or gelled sample. In this case, the cup has a refractive index of less than that of the sample it is intended to contain. As an example, in this configuration, the sample may be an ionic liquid with a refractive index that is generally more than 1.4. The material constituting this cup may thus be a polymer with an index of less than 1.4 in the form of a hollow block of substantially hemispherical cups, or indeed a thin thermoformed film. In both cases, the cups may be sealed by attaching a transparent lid forming the surface SS.

After spraying, the slip cover SS is upturned over a frame formed with the aid of double sided adhesive tape RDF, for example of the "gene frame" type (250 µm thick), which has been deposited on another slip cover L. The adhesive tape then forms walls between the slip cover SS and the slip cover S. Thus, a thin sealed chamber is formed that prevents evaporation of the droplets. A heating means MC is used to maintain this chamber at a constant temperature of 37° and the assembly is mounted on a motorized platen PM. A microscope MS is used to observe the droplets from the side of the upper slip cover SS. Preferably, illumination and collection of light produced by the sample are carried out from the same side with respect to the slip cover SS. Thus, illumination of the sample can also benefit from the effect of confinement in a "bowl of light", but this is not essential.

Observations can be made using an imaging system comprising an objective LO (for example: magnification 10, numerical aperture 0.5) and a camera CM for image acquisition. In FIG. 6, the reference SO in general indicates the other components of the imaging system (illuminating means, dichroic mirrors, filters, etc.), which are variables and depend on the observation technique employed. In fact, the principle of the invention can be applied to several different observation techniques, as will be described in more detail below with the aid of FIGS. 7A to 12. Clearly, this list of embodiments is not exhaustive. For the purposes of simplicity, these FIGS. 7A to 12 do not show the optical system or the imagery used for implementing the method.

Figure 7A:
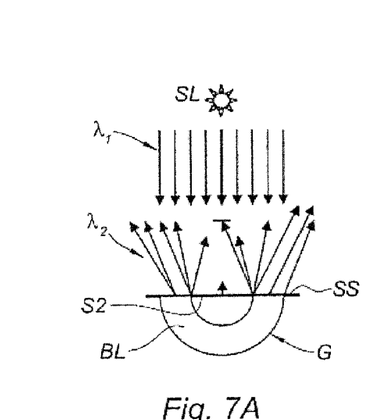
FIGS. 7A and 7B respectively show the schematic for a method in accordance with a first embodiment of the invention and an image acquired using this method.

FIG. 7A illustrates, in a highly diagrammatic manner, the application of the method of the invention to the detection of a fluorophore in droplets by epifluorescence microscopy. Excitation light with a wavelength $\lambda_1$ is emitted by a source SL (typically a mercury lamp or halogen lamp provided with a filter) and injected into the droplet G via its surface S2 that adheres to the substrate SS. This light, which is partially confined in the "bowl of light" BL, induces fluorescence of the fluorophore, which emits radiation at a wavelength $\lambda_2 > \lambda_1$.

Figure 7B:
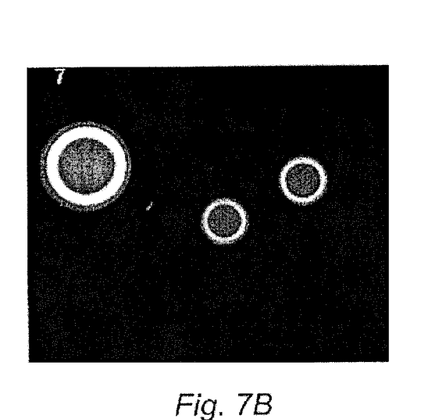

As can be seen in FIG. 7B, the fluorescence radiation leaves the droplet and the substrate, having been partially concentrated into a luminous ring. It will be noted that the molecules of fluorophore that are outside the bowl of light contribute less effectively to the signal detected by the camera, as they are exposed to a flux of excitation light that is less intense and the photons they emit are not confined within the luminous ring. The "bowl of light" occupies a fraction of the volume of the droplet that is greater with increased magnitude of the ratio $n_{int}/n_{ext}$.

The images of FIG. 7B were obtained by exciting a solution of the fluorophore 4MU in MOPS buffer (3-(N-morpholino)propanesulfonic acid) at a wavelength $\lambda_1 = 360$ nm. The fluorescence radiation was isolated by a filter centered on $\lambda_2 = 450$ nm.

In a variation, the droplet can be illuminated via the surface S1, resulting in spatially more homogeneous excitation in the drop, to the detriment of the effect of confinement of the excitation beam in a bowl of light. In this case, it is no longer possible to use the term "epifluorescence".

The observation method of FIGS. 7A and 7B may in particular be applied to the study of the kinetics of chemical or biochemical reactions.

Figure 8A:
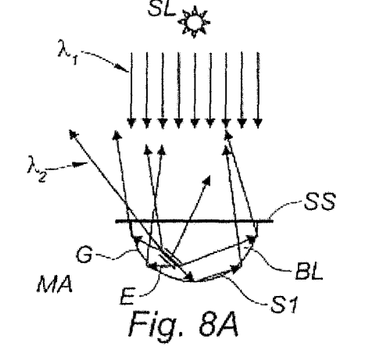
FIGS. 8A and 8B respectively show the schematic for a method in accordance with a second embodiment of the invention and an image acquired using this method.
Figure 8B:
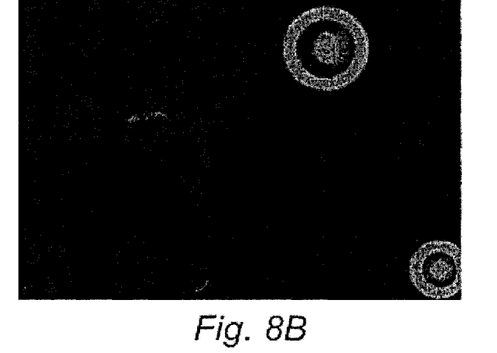

FIGS. 8A and 8B refer to the case of observation, still using epifluorescence microscopy, of a fluorescent object with microscopic dimensions E, such as a bacterium, genetically modified if appropriate. If the object E is more dense than the liquid forming the droplet, it will fall towards the lower end thereof and then position itself inside the "bowl of light". Confining the excitation light close to the surface S1 thus proves to be particularly advantageous. FIG. 8B shows both the ring in which the light radiation emitted by the object E is concentrated and guided by the droplet/ambient medium interface, and the image of said object formed by the "direct" radiation, which passes through the substrate without prior reflection by the surface S1.

In the case of this FIG. 8B, the object E is a genetically modified *Escherichia coli* bacterium in growth medium containing MUG (4MU glucuronate). The observations were made at $\lambda_1 = 557$ nm (excitation wavelength) and $\lambda_2 = 579$ nm (fluorescence wavelength).

An observation method in accordance with FIGS. 8A and 8B may be applied to counting bacteria inoculated into a solution that is sprayed as described above to form a series of droplets on a microscope slide, the bacteria being distributed in a random manner in the droplets. The solution may comprise a reference fluorophore, for example FITC (fluorescein isothiocyanate), which means that the drops can be counted, their volume estimated and the fluorescence signal from the bacteria normalized in order to cancel out instrumental drift.

This method was tested using a strain of *Escherichia coli*, ATCC 11775, which is a β-glucoronidase-positive strain. Enzymatic glucuronidase activity can be used to degrade the fluorogenic substrate MUG, which causes the release of the fluorophore 4MU. The aqueous solution into which these bacteria were inoculated was a buffer containing MOPS (3-(N-morpholino)propanesulfonic acid), the fluorogenic substrate MUG as well as FITC as the reference fluorophore. The composition of this medium was:

MOPS (4-morpholinopropanesulfonic acid, sodium salt), 150 mM;
magnesium sulfate 2.6 mM;
sodium glucuronate, 854 µM;
methyl β-d-glucuronide, 870 µM;
MUG (4-methylumbelliferyl-β-d-glucuronide), 113 µM;
fluorescein, 4.15 µM.

The droplets were observed using an AxioImager microscope from Zeiss with an objective corrected for the thickness of the slide, ×10, NA 0.5. The MUG acted as a marker for each bacterium because of the production of 4MU fluorophore in the droplets containing at least one bacterium. The fluorophore FITC acted as a marker for each drop, because each drop emits it independently of the presence of a bacterium.

Since the fluorophore 4MU is produced by the metabolism of the bacteria, its fluorescence signal increases with time. Further, the buffer contains a given concentration of the fluorophore FITC, which remains constant throughout the measurement: the fluorescence signal from FITC is thus constant and can be used as the reference signal.

During the observation:
the sample is alternately excited at the FITC and at the 4MU fluorophore excitation wavelengths (to be completed)
images corresponding to the emission wavelengths of the FITC and the fluorophore 4MU are recorded alternately;
the drops, which are all fluorescent, are localized on each FITC emission image, each drop producing a ring on the image. Each ring defines a spatial zone of interest corresponding to each drop. On the other hand, the outer radius, Rext, of each ring of a given image can be measured, this radius being correlated to the volume of each drop using the following expression:

$$V(R_{ext}, \theta_{cont}) = \frac{\pi}{3}\left(\frac{R_{ext}}{\sin(\theta_{cont})}\right)^3 (2 - 3\cos(\theta_{cont}) + \cos^3(\theta_{cont}))$$

where:
$\theta_{cont}$—contact angle of drop on slip cover SS;
$R_{ext}$=external diameter of luminous ring.

Pre-defined spatial zones of interest are used on each 4MU fluorophore emission image. The mean intensity of the signal from pixels constituting each spatial zone of interest is determined, this mean intensity being the mean intensity of the signal produced by each drop. Optionally, the mean intensity of the signal produced by each drop can be normalized, at the emission wavelength of the fluorophore 4MU, by the mean intensity of the signal corresponding to the same drop, at the emission wavelength of FITC. By thresholding the intensity, or the normalized intensity, the drops containing at least one bacterium are determined, thresholding allowing a decision to be made regarding the presence or absence of at least one bacterium in the drop.

By applying a Poisson's law, the most probable concentration of bacteria (CPP) in the initial solution can be determined, i.e. the solution dispersed in the form of drops.

It can be demonstrated that:

$$\sum_{j/occupieddrop} \frac{Vj}{1 - e^{-CPP.Vi}} = \sum_{i/observeddrop} Vi$$

Vj is the elementary volume of each drop j occupied by at least one bacterium;
Vi is the elementary volume of each drop i observed by FITC fluorescence;
CPP is the most probable concentration of bacteria in the initial solution. The dimension of this concentration is the inverse of volume.

In a test, a value of $5.7 \times 10^5$ bacteria/mL was determined in less than 4 hours. The exact concentration of bacteria was not known, and so a CPS3 dish count (supplier: bioMérieux) was carried out after more than 24 hours culture as a reference. This counting method provided a result of $6.5 \times 10^5$ bacteria/mL. This result was in good agreement with the reference method, since the observed variation was in fact less than the factor of 2 that is generally acceptable.

Figure 9A:
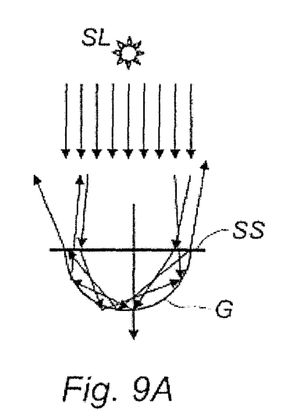
FIGS. 9A and 9B respectively show the schematic for a method in accordance with a third embodiment of the invention, an image acquired using this method and a detail of such an image.
Figure 9B:
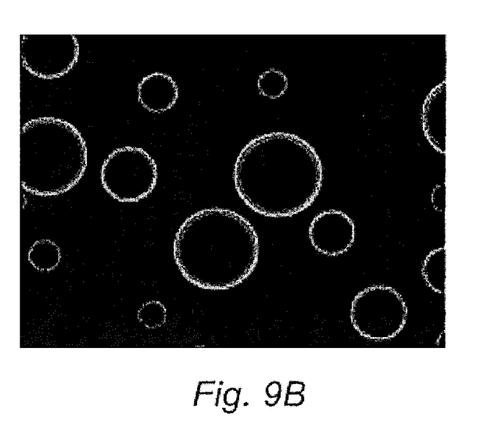

FIGS. 9A and 9B show images of droplets observed by reflection microscopy (illumination and detection through the substrate SS at the same wavelength $\lambda$). This may be used, for example, to verify the function of microfluidics devices, to study the wettability of the substrate or to study the refractive index of the liquid forming the droplet.

Figure 10:
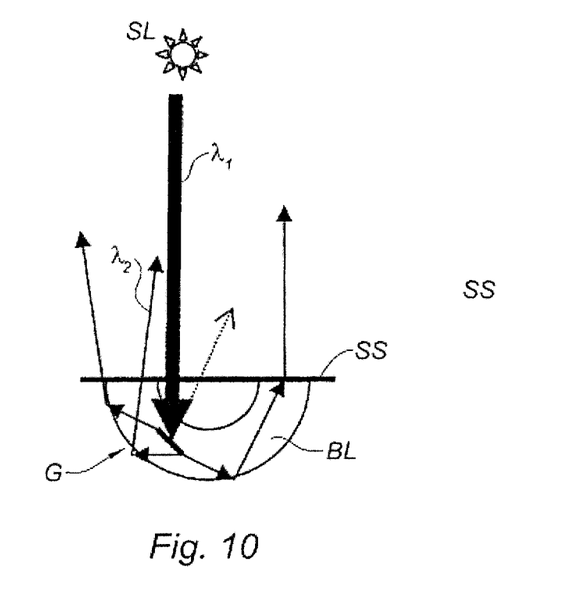
in FIG. 10, the schematic for a method in accordance with a fourth embodiment of the invention.

The light guidance that occurs at the interface between the droplet and the ambient medium may be exploited in order to provide increased sensitivity using optical spectroscopic methods (for example intrinsic fluorescence and inelastic Raman diffusion) when observing biological objects or analytes. For analytes, a configuration identical to fluorescence is used (FIG. 7A). For single objects E, both the fluorescence configuration (FIG. 8A) may be used and also a novel configuration in which the excitation light is limited to a pencil beam impacting the object (see FIG. 10).

All of the observation methods described so far involve illuminating the sample, either through the convex surface S1 or—which is generally preferable—through the planar surface S2. However, illumination of this type is not necessary when the sample is luminescent, which is the case with some microorganisms or some solutions in which chemical reactions occur causing the emission of light (chemoluminescent reactions catalyzed by enzymes such as alkaline phosphatase or horseradish peroxidase, or modified microorganisms comprising a luciferase activity as described, for example, in the article by M L Eldridge et al, "*Saccharomyces cerevisiae* BLYAS, a New Bioluminescent Bioreporter for Detection of Androgenic Compounds", APPLIED AND ENVIRONMENTAL MICROBIOLOGY 73(19), p 6012-6018 (2007). Simulations were carried out in order to compare the light signal detected by a detector placed at a distance from a drop, collecting the light signal produced inside the latter in a uniform and isotropic manner in the following two configurations:
a hemispherical drop as shown in FIG. 3A, the drop being formed by an aqueous solution comprising a given concentration of chemiluminescent molecule;
a spherical drop with the same volume and the same composition immersed in an oil bath in the configuration shown in FIG. 4A.

According to the calculations, the signal collected is 2.5 to 2.8 times higher when the drop is hemispherical for numerical apertures of the detector in the range 0.1 to 0.6. Thus, the hemispherical configuration to produce a more intense signal.

Figure 11:
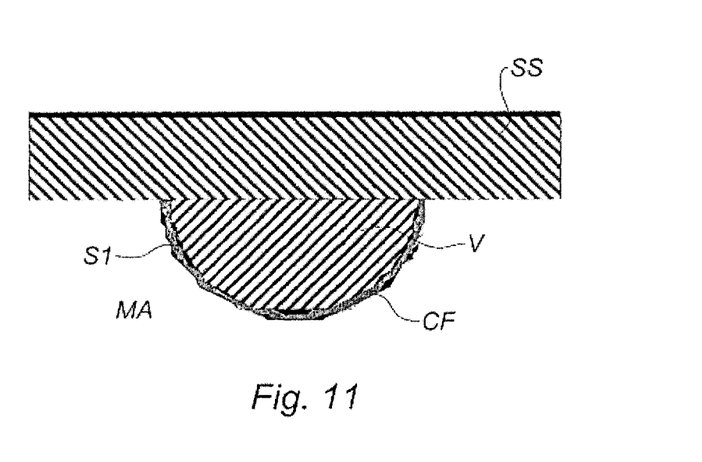
in FIG. 11, the schematic for a method in accordance with a fifth embodiment of the invention.

FIG. 11 pertains to a particular case in which a solid protuberance V with a hemispherical shape (a "half-bead") and having a functionalized layer CF deposited on its surface S1 is used as a chemical sensor. Chemical species forming or contained in the ambient medium MA (liquid or gaseous) react with the functionalized layer CF to produce a detectable optical signal such as a fluorescence or luminescence signal, or to modify the refractive index thereof, which in turn affects the internal radius of the luminous ring (observation in the configuration of FIG. 9A). In a variation, the material itself constituting the protuberance V might react with the ambient medium. In this case, the protuberance may be replaced by a droplet, or be constituted by a gel.

The invention claimed is:

1. A method for observing a sample, comprising the steps of:
   a) providing a volume of a substantially transparent medium having a first refractive index ($n_{int}$) and having a first convex, rounded or facetted surface, wherein the angular deviation of the surface with respect to a sphere with center C is less than 12.5° or wherein the facetted surface comprises at least 10 facets, and a second substantially planar surface, said first surface separating said volume from an ambient medium having a second refractive index ($n_{ext}$) that is lower than said first index, the sample to be observed being contained in said volume or disposed within said volume or deposited on said first surface;
   b) observing said sample through said second substantially planar surface; and
   c) determining the presence of a substance or an object in the sample by detection during said step b) of a luminous ring matched to said volume.

2. The method as claimed in claim 1, in which said volume has a substantially hemispherical shape.

3. The method as claimed in claim 1, in which said step c) comprises determining the presence of a microorganism in said sample.

4. The method as claimed in claim 1, in which said volume is a droplet adhered to a transparent substrate forming said second substantially planar surface.

5. The method as claimed in claim 4, in which:
   said step a) comprises producing a plurality of droplets forming said volumes at least some of which contain at least one object or a substance to be detected; and
   said step b) comprises simultaneously observing a plurality of said droplets.

6. The method as claimed in claim 1, in which said volume is formed from a material that is sensitive to an analyte contained in said ambient medium.

7. The method as claimed in claim 1, in which said ambient medium is air.

8. The method as claimed in claim 1, in which said step b) comprises an operation for illuminating said volume with a light source.

9. The method as claimed in claim 8, in which said illumination is carried out either through said convex, rounded or facetted first surface or through said substantially planar second surface.

10. The method as claimed in claim 8, in which said step b) comprises detecting a fluorescence signal.

11. The method as claimed in claim 10, in which said step b) is carried out by epifluorescence microscopy.

* * * * *